US008075473B2

United States Patent
Rudi

(10) Patent No.: US 8,075,473 B2
(45) Date of Patent: Dec. 13, 2011

(54) EXTENSION DEVICE FOR PERMANENT PENIS ENLARGEMENT AND STRAIGHTENING

(75) Inventor: Johann Rudi, Waldbröl (DE)

(73) Assignee: MSP Concept GmbH & Co. KG, Berlin (DE)

( * ) Notice: Subject to any disclaimer, the term of this patent is extended or adjusted under 35 U.S.C. 154(b) by 309 days.

(21) Appl. No.: 12/308,527

(22) PCT Filed: Jun. 18, 2007

(86) PCT No.: PCT/DE2007/001097
§ 371 (c)(1),
(2), (4) Date: Dec. 17, 2008

(87) PCT Pub. No.: WO2008/000226
PCT Pub. Date: Jan. 3, 2008

(65) Prior Publication Data
US 2010/0016656 A1    Jan. 21, 2010

(30) Foreign Application Priority Data

Jun. 26, 2006  (DE) .......................... 10 2006 029 258
Jun. 1, 2007   (DE) .......................... 10 2007 026 063

(51) Int. Cl.
     *A61F 5/00*         (2006.01)
(52) U.S. Cl. ...................................................... 600/38
(58) Field of Classification Search .............. 600/38–41; 128/897, 898
     See application file for complete search history.

(56) References Cited

U.S. PATENT DOCUMENTS

| 4,690,135 A | | 9/1987 | Gerow | |
|---|---|---|---|---|
| 4,790,296 A | * | 12/1988 | Segal | 601/97 |
| 5,707,341 A | * | 1/1998 | Mathewuse | 600/39 |
| 5,836,864 A | * | 11/1998 | Clark, Jr. | 600/38 |
| 6,416,460 B1 | * | 7/2002 | Jochum | 600/39 |
| 7,802,577 B2 | * | 9/2010 | Cvetanovic | 128/845 |
| 2007/0093687 A1 | | 4/2007 | Hoefer | |

FOREIGN PATENT DOCUMENTS

| CA | 2 444 663 | 3/2005 |
|---|---|---|
| DE | 100 01 331 | 7/2001 |
| DE | 20 2005 017 165 | 3/2006 |
| EP | 1 023 013 | 8/2000 |
| EP | 1 779 822 | 5/2007 |
| FR | 1 605 238 | 8/1973 |
| WO | WO 87/06821 | 11/1987 |

* cited by examiner

*Primary Examiner* — Samuel Gilbert
(74) *Attorney, Agent, or Firm* — Collard & Roe, P.C.

(57) ABSTRACT

Disclosed is an extension apparatus for enlarging and straightening a penis. The extension apparatus includes a fastening device (1) that is mounted on the penis, and a tension device (8) which is connected to the fastening device (1). The fastening device is provided with a dimensionally stable receiving member (2) which positively accommodates the entire area of the glans penis and whose inner contour essentially matches the shape of the glans penis. The fastening device can be connected to a device for supplying and sucking air and adjoins an elastic tubular seal (15) at the opening (3) provided for introducing the glans penis. The simple apparatus, which is suitable also for short penis lengths, can be put on quickly and in an uncomplicated manner, provides a high degree of comfort during wearing and optimum tensile strength, resulting in a gentle extension treatment that has no major side effects for the user.

8 Claims, 2 Drawing Sheets

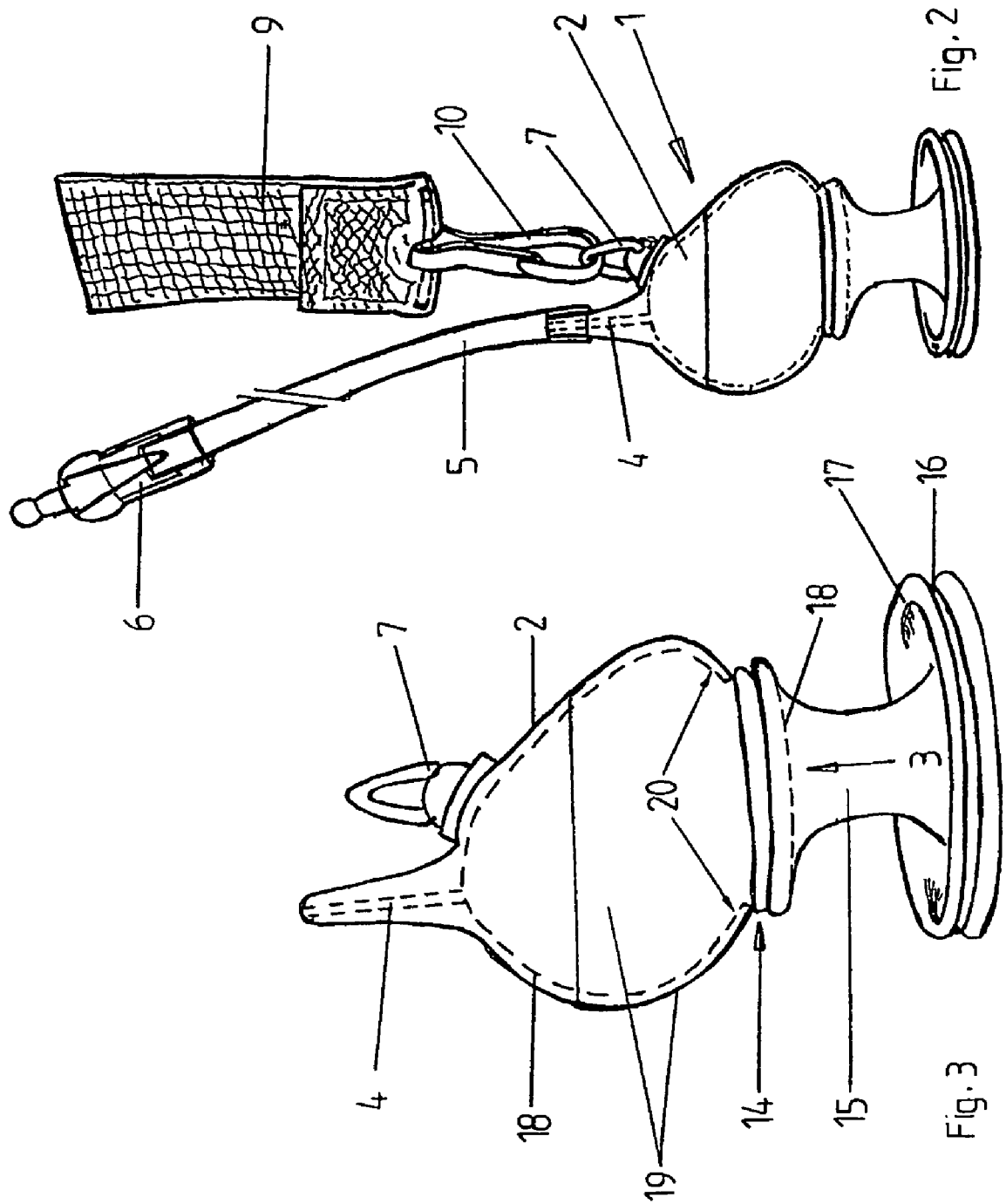

EXTENSION DEVICE FOR PERMANENT PENIS ENLARGEMENT AND STRAIGHTENING

CROSS REFERENCE TO RELATED APPLICATIONS

This application is the National Stage of PCT/DE2007/001097 filed on Jun. 18, 2007, which claims priority under 35 U.S.C. §119 of German Application No. 10 2006 029 258.8 filed on Jun. 26, 2006 and German Application No. 10 200.7 026 063.8 filed Jun. 1, 2007. The international application under PCT article 21(2) was not published in English.

The invention relates to an extension device for permanent penis enlargement and straightening by means of long-term elongation, the fastening means applied to the penis and a pulling apparatus connected to the fastening means.

A penis extension device of the type mentioned above is described for example in EP 1 023 013. The pulling means for exerting a pulling action on the front end of the penis is here a flexible strap which is elastic or adjustable in length, is held on the root of the penis by means of an annular cuff, is placed around the user's body and the free end of which is connected to the penis by means of a fastening means in the form of a saucer-shaped slide and a small band. Due to the pulling force exerted on the tip of the penis by the strap which is held on the root of the penis as an abutment, the penis is elongated and permanently enlarged and if appropriate straightened in the process. This type of fastening proves disadvantageous in several aspects. In particular, painful pressure sores can develop in the case of the pulling forces which are usually to be applied, so that a long-term elongation treatment is not guaranteed.

A fastening means which is known from DE 100 01 331 A1 comprises a condom-like cylindrical cap which is made from highly elastic material and can be pulled completely over the glans penis, which cap has a connection element in its front region for coupling to the pulling means and has an annular section which is suitable for sealed bearing on the penis shaft directly behind the glans penis in its rear region, which annular section acts as a sealing element. Due to the pulling force acting on the front region and the sealing on the penis shaft, a vacuum should be generated, on the basis of which and the elastic configuration as well as an additional adhesive coating or a double-sided adhesive strip the fastening means is held securely and gently on the penis. In the case of the fastening means, which is to be put on with considerable outlay on account of the adhesive, an increase in volume of the glans penis achieved by means of the vacuum brings about a high contact pressure around the circumference of the glans penis and therefore an impairment of blood flow. The non-positive fastening on the penis, which is brought about by means of high frictional and adhesive forces, leads to swellings and as a result thereof to lymph fluid passing out of the tissue.

Methods for stretching and elongating the penis by applying a pulling force and therefore for achieving an increase in size have, in addition, been used for a long time, for example in the case of primitive peoples by attaching weights.

The object of the invention is to develop extension device for penis enlargement and straightening which is of simple construction and can be put on with minimum outlay and guarantees a secure and gentle fastening on the penis as well as a high degree of wear comfort.

This object is achieved according to the invention with a penis extension device configured according to the features of the Patent Claim 1. Advantageous developments of the invention result from the subclaims.

The basic principle of the invention consists in the fact that the fastening means for transmitting the pulling force exerted by a pulling apparatus to the penis comprises a dimensionally stable and essentially rigid accommodation body which accommodates the glans penis positively, the inner contour of which accommodation body essentially corresponds to the shape of the glans penis, which accommodation body can be connected via a closure valve to a pump for generating an air pressure difference, specifically by supplying or sucking out air when placing or inserting the glans penis and when holding it in the accommodation body under a small vacuum with the closure valve closed, and to the opening of which accommodation body, provided for inserting the glans penis, a tube seal connects.

On account of the positive, essentially all-over connection between fastening means and glans penis, a high and long-lasting, but nonetheless gentle force action can be exerted without needing to fear damage to health, pressure sores or pains. The vacuum acts first to facilitate the insertion, but also during the elongation treatment in such a manner that the fastening means always bears in a sealed manner against the entire surface of the glans penis, so that even in the case of a small vacuum, a constant retention force acts only on the glans penis and as a result of the small vacuum and the fastening means, which is adapted to the shape and size of the glans penis, no over-elongation of the tissue with the associated consequences takes place. The vacuum is only so big that the fastening means, which is adapted to the shape and size of the glans penis, actually bears against the entire surface of the glans penis in order to create a secure and gentle connection to the glans penis by means of positive fit and adhesion. The apparatus can be put on in a simple manner and comfortably and guarantees a high degree of wear comfort. As only the glans penis is needed for mounting, the device is advantageously also suitable for use in the case of very small penises.

In accordance with the different shape and size of the glans penis, accommodation bodies which are configured differently with respect to the inner contour are provided.

On the other hand, it is possible when using only one uniformly configured accommodation body to provide inserts which are adapted to the shape and size of the accommodation body and which can be inserted into the accommodation body and which can also be configured to be self adjusting.

According to a further important feature of the invention, the opening for inserting the glans penis into the accommodation body can be sealed with an elastic membrane which, in the process of inserting the glans penis, envelops the entire surface of the glans penis under vacuum and, independently of the shape and size of the glans penis, creates the complete and gently acting positive fit with the glans penis within the accommodation body.

The membrane can, on account of its elasticity, compensate individual changes in the shape and size of the glans penis arising during use, so that in all eventualities a constant retention action is guaranteed.

In further configuration of the invention, a lubricant is provided on the inner surfaces of the tube seal and the accommodation body or the insert or the membrane, which lubricant on the one hand serves easy insertion and on the other hand creates a particularly integral adhesively-acting connection between glans penis and accommodation body or insert or membrane.

According to yet another feature of the invention, a support ring is attached at the free end of the tube seal which is fastened to the accommodation body, the internal diameter of which support ring is dimensioned approximately correspondingly to the penis diameter. This simplifies the insertion of the glans penis and prevents the tube seal from slipping into the accommodation body.

An elastic retaining bead can be formed at the ends of the tube seal for the latter's secure fastening to the accommodation body and to the support ring.

The tube seal and the membrane can be produced from the tube-like spout and the balloon section of a conventional balloon of a corresponding size.

An air nozzle provided with a closure valve which is moulded on the accommodation body is used for creating the vacuum. Air can be sucked out in a dosed manner, for example with a pump, via the closure valve.

In the case of a membrane used in connection with the accommodation body an elastic elongation (bulging) of the membrane can take place directly before the insertion of the glans penis by supplying air to the accommodation body via the air nozzle to improve the contact with the glans penis, in order, as a result, to guarantee a contact without air inclusions between glans penis and membrane.

The pulling apparatus required to exert a pulling force acting on the accommodation body comprises a tightening strap which is adjustable in length or elastic and which on the one hand is connected to the accommodation body, for example a coupling element integrated into the closure valve, and on the other hand is connected by means of fastening clips or directly to a strap or support on the body of the user, a belt, braces or another part of the clothing. Even attaching a weight to the accommodation body is conceivable. The pulling force on the accommodation body can also be exerted via a frame supported on the body of the user, which frame is adjustable in length.

An exemplary embodiment of the invention is described in more detail with the aid of the drawing. In the figures:

FIG. 2 shows a detailed representation of the extension device according to FIG. 1; and FIG. 3 shows an enlarged representation of the fastening means according to FIG. 2.

Figure 1:
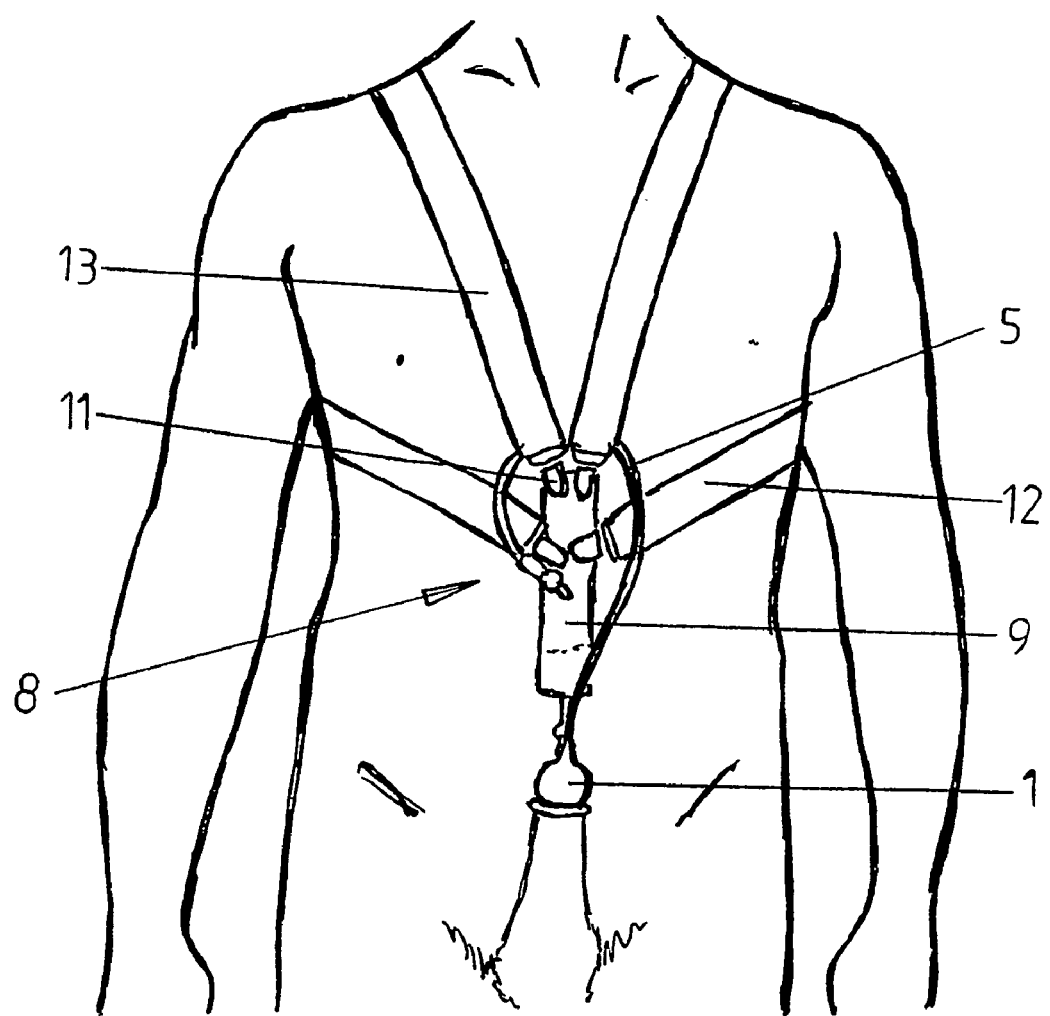
FIG. 1 shows an extension device which has been put on the user and which consists of a pulling apparatus and a fastening means.

The fastening means 1 comprises an accommodation body 2 which consists of an essentially rigid material and completely envelops the glans penis, the inner contour of which accommodation body essentially corresponds to the shape and size of the engorged glans penis. The accommodation body 2 has a wide opening 3 which faces the penis shaft and has an air nozzle 4 on the side opposite to that, to which air nozzle a flexible air line 5 is connected with a closure valve 6 attached at its free end. A coupling ring 7, which essentially lies opposite the opening 3, for producing the connection between the fastening means 1, that is to say the accommodation body 2, and the pulling means 8, which exerts a pulling force on the accommodation body 2 and therefore on the penis, is additionally attached to the exterior of the accommodation body 2.

The pulling means 8 comprises a tightening belt 9 which is flexible, elastic or adjustable in length and is connected on the one hand to the accommodation body 2, here via a carabiner 10 and the coupling ring 7, and on the other hand via fastening clips 11 to a strap 12 or support 13 held on the body of the user. The fastening of the tightening strap 9 can equally take place on a belt or braces, if appropriate even on a piece of clothing (in each case not represented). It is, however, also conceivable that the pulling action on the accommodation body 2 is generated by a weight (not represented) fastened to the coupling ring 7.

In the region of the opening 3, the accommodation body 2 is shaped in such a manner that a circumferential retaining groove 14 for fastening a tube seal 15 is formed on its outer circumference. The slightly sloped edge region which is adjacent to the opening 3 in the interior of the accommodation body 2 is a circumferential stop surface 20 which acts on the circumferential surface formed on the lower edge of the glans penis when the extension device is being used. As a result, a positive connection is produced between the accommodation body 2 and the glans penis accommodated in it, which positive connection guarantees a secure transmission of force by means of positive fit (and not by means of static friction).

One end of the tube seal 15 which consists of an elastic material and has a retaining bead at each of its ends is elastically retained in the retaining groove 14 of the accommodation body 2. The other end of the tube seal 15 is fixed in the circumferential groove 16 of a support ring 17.

When using the extension device, the glans penis is inserted into the accommodation body 2 via the tube seal 15, whereby a lubricant for facilitating the insertion can be applied to its inner surface, as can additionally also be applied to the membrane 18 described further below or in the accommodation body 2 to improve the adhesive action. The support ring 17, the diameter of which is dimensioned approximately correspondingly to the penis width, enables a simple insertion of the glans penis and additionally prevents the tube seal 15 from slipping into the accommodation body 2. During the insertion, a slight vacuum is additionally generated in the accommodation body 2, which is sealed by means of the tube seal 15, by sucking out air at the closure valve 6, which vacuum facilitates the insertion of the glans penis until it bears against the inner contour of the accommodation body 2. The exterior surface of the glans penis now bears, preferably with interposition of the above-mentioned lubricant, with its entire surface against the inner surface of the accommodation body 2 which is closed in a sealed manner on both sides by means of the closure valve 6 and tube seal 15, so that a positive connection exists between the glans penis and the accommodation body 2 and the pulling forces acting on the accommodation body 2 can be transmitted securely, evenly and gently, preferably via a skin friendly adhesively acting lubricant, to the glans penis and therefore to the penis. As the surface of the glans penis bears over the entire surface against the inner contour of the accommodation body 2 and only a small vacuum acts on the glans penis to maintain the positive fit, undesirable side effects are prevented. The vacuum is used only for the easier insertion of the glans penis and for its positive contact with the inner surface of the accommodation body 2, which contact is improved by adhesion forces due to the lubricant used. The vacuum does not however act as primary retention force.

The shape and size of the glans penis can differ for different users, so that, as long as no membrane is used, consequently accommodation bodies 2 or inserts in various sizes should be kept ready in order to guarantee an all-over positive contact with the glans penis in the case of a small vacuum which does not act directly on the glans penis.

As the FIGS. 2 and 3 show, independently of the respective size of the glans penis, with one and the same accommodation body 2, but using an elastically deformable membrane 18, an inner contour of the accommodation body 2 can nonetheless however be achieved which makes all-over contact with the glans penis. The membrane 18 is formed by a rubber balloon 19 which is pulled over the accommodation body 2 and thereby shuts the latter's opening 3. Only after the rubber balloon 19 is pulled over the accommodation body is the tube seal 15 attached to the accommodation body 2. Before inserting the glans penis, the membrane 18 is bulged outwards by means of supplying air to the accommodation body 2 for a short period of time via the closure valve 6 in order to bring about an integral contact with the glans penis during the insertion. When inserting the glans penis whilst at the same time generating a vacuum by sucking out air at the closure valve 6 by means of a pump (not represented), the membrane 18 is sucked into the accommodation body 2 via the opening 3, together with the glans penis and bearing against the surface of the latter. As a result, it is ensured that a glans penis, which can also be markedly smaller than the inner volume of the accommodation body 2 and can also have a shape different from the latter's inner contour, is enveloped all over on its entire external surface, preferably with the interposition of a lubricant which acts adhesively here, and is fixed positively in the accommodation body 2, specifically without the vacuum generated during insertion acting directly on the glans penis.

The accommodation body 2 with air nozzle 4 is formed integrally from rigid or substantially rigid material, for example plastic, hard rubber or the like.

REFERENCE LIST

1 Fastening means
2 Accommodation body
3 Opening of 2
4 Air nozzle
5 Air line
6 Closure valve
7 Coupling ring
8 Pulling apparatus
9 Tightening strap of 8
10 Carabiner
11 Fastening clip
12 Strap
13 Support
14 Retaining groove of 2
15 Tube seal
16 Circumferential groove of 17
17 Support ring
18 Membrane
19 Rubber balloon
20 Circumferential stop surface

The invention claimed is:

1. An extension device for permanent penis enlargement and straightening via long-term elongation, the extension device comprising:
a fastening means for application to a penis, the fastening means having an accommodation body, the accommodation body:
being dimensionally stable,
accommodating a glans penis of the penis over the entire surface of the glans penis when the glans penis is inserted into the extension device,
having an inner contour essentially corresponding to a shape of the glans penis,
having an opening for allowing insertion of the glans penis, and
having an inner surface;
a pulling apparatus connected to the fastening means; an elastic tube seal connected to the opening of the accommodation body; and
a lubricant located on the inner surface of the accommodation body;
wherein the pulling apparatus is formed by:
a support, strap, belt or other clothing accessory or piece of clothing, the support, strap, belt or other clothing accessory or piece of clothing being connected to the accommodation body, being held on a body of the user, and being used as a stop,
a stationary object,
a frame supported on a body of the user, the frame being adjustable in length, or
a weight attached to the accommodation body.

2. An extension device for permanent penis enlargement and straightening via long-term elongation, the extension device comprising:
a fastening means for application to a penis, the fastening means having:
an accommodation body with an opening for allowing insertion of a glans penis of the penis, and
an elastic membrane attached to the accommodation body over the opening,
the accommodation body:
being dimensionally stable,
accommodating a glans penis of the penis over an entire surface of the glans penis when the glans penis is inserted into the extension device, and
having an inner contour essentially corresponding to a shape of the glans penis in that the elastic membrane is bulgable outwards under an action of an overpressure and can be drawn in under an action of a vacuum when the glans penis is inserted into the accommodation body, and
when the glans penis is inserted into the opening, the elastic membrane enveloping the glans penis positively over an entire surface of the glans penis independently of a respective shape and size of the glans penis;
a pulling apparatus connected to the fastening means; and
an elastic tube seal connected to the opening of the accommodation body.

3. The extension device according to claim 2, wherein the elastic tube seal is formed from a spout section, and
wherein the elastic membrane is formed from a balloon section of a commercially available balloon of corresponding size, the balloon section being pulled over the accommodation body.

4. An extension device for permanent penis enlargement and straightening via long-term elongation, the extension device comprising:
a fastening means for application to a penis, the fastening means having an accommodation body, the accommodation body:
being dimensionally stable,
accommodating a glans penis of the penis over an entire surface of the glans penis when the glans penis is inserted into the extension device,
having an inner contour essentially corresponding to a shape of the glans penis, and
having an opening for allowing insertion of the glans penis;
a pulling apparatus connected to the fastening means;
an elastic tube seal connected to the opening of the accommodation body, the elastic tube seal having an inner surface;
a lubricant located on the inner surface of the elastic tube seal; and
a support ring dimensioned approximately correspondingly to a penis diameter of the penis for simple insertion of the glans penis,
wherein a first end of the elastic tube seal is at a distance from the accommodation body and is connected to the support ring.

5. The extension device according to claim 4, wherein the elastic tube seal is elastically fixed at the first end in a circumferential groove of the support ring; and wherein the elastic tube seal is elastically fixed at a second end of the elastic tube seal in a retaining groove formed on the accommodation body.

6. The extension device according to claim 5, wherein the elastic tube seal has an elastic retaining bead at least one of the first and second ends.

7. An extension device for permanent penis enlargement and straightening via long-term elongation, the extension device comprising:

a fastening means for application to a penis, the fastening means having an accommodation body, the accommodation body:
  being dimensionally stable,
  accommodating a glans penis of the penis over an entire surface of the glans penis when the glans penis is inserted into the extension device,
  having an inner contour essentially corresponding to a shape of the glans penis, and
  having an opening for allowing insertion of the glans penis;

a pulling apparatus connected to the fastening means;

an elastic tube seal connected to the opening of the accommodation body; and means for supplying air to and sucking out air from the accommodation body, the means for supplying and sucking out air from the accommodation body being for generating an overpressure or vacuum and comprising a closure valve provided on the accommodation body, the closure valve being connectable to an air suction and pressure pump.

8. The extension device according to claim 7, further comprising a coupling element on the accommodation body, the coupling element being on a side of the accommodation body opposite from the opening;

wherein the coupling element can be coupled to the pulling apparatus.

* * * * *